(12) United States Patent
Wenger et al.

(10) Patent No.: US 9,943,350 B2
(45) Date of Patent: *Apr. 17, 2018

(54) MEDICAL APPARATUS, AND SURGICAL METHOD

(71) Applicant: SpineWelding AG, Schlieren (CH)

(72) Inventors: Andreas Wenger, Muri b. Bern (CH); Jörg Mayer, Niederlenz (CH)

(73) Assignee: SPINEWELDING AG, Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/824,376

(22) Filed: Aug. 12, 2015

(65) Prior Publication Data

US 2015/0342658 A1 Dec. 3, 2015

Related U.S. Application Data

(62) Division of application No. 13/508,393, filed as application No. PCT/CH2010/000279 on Nov. 9, 2010, now Pat. No. 9,131,961.

(Continued)

(51) Int. Cl.
*A61B 17/86* (2006.01)
*A61B 17/88* (2006.01)
(Continued)

(52) U.S. Cl.
CPC .... *A61B 17/8811* (2013.01); *A61B 17/00491* (2013.01); *A61B 17/68* (2013.01); *A61B 17/686* (2013.01); *A61B 17/7001* (2013.01); *A61B 17/7032* (2013.01); *A61B 17/7098* (2013.01); *A61B 17/863* (2013.01); *A61B 17/864* (2013.01); *A61B 17/8822* (2013.01); *A61B 17/8894* (2013.01); *A61C 8/0012* (2013.01); *A61C 8/0033* (2013.01);
(Continued)

(58) Field of Classification Search
CPC .......................... A61B 17/7098; A61B 17/864
See application file for complete search history.

(56) References Cited

U.S. PATENT DOCUMENTS

| 8,057,480 B2 | 11/2011 | Dorawa et al. |
| 2009/0018471 A1* | 1/2009 | Dorawa ......... A61B 17/320068 601/2 |
| 2010/0256688 A1* | 10/2010 | Giersch .................. A61B 17/68 606/305 |

FOREIGN PATENT DOCUMENTS

| WO | 2007/014142 | 2/2007 |
| WO | 2009/010234 | 1/2009 |

* cited by examiner

*Primary Examiner* — Samuel Hanna
(74) *Attorney, Agent, or Firm* — Rankin, Hill & Clark LLP

(57) ABSTRACT

A method for automated implantation of an implant or for an automated augmentation process of hard tissue and/or hard tissue replacement material using a sheath element is provided. The implantation apparatus includes a casing, a converter operable to generate mechanical vibrations the converter inside the casing and displaceable in a longitudinal direction relative to the casing, and a sonotrode coupled to an output location of the converter. A shaft portion with a retention structure is rotationally coupled to the casing and is equipped for cooperating with a rotationally asymmetric element of the sheath element to rotationally couple the casing to the sheath element. An axial coupling is equipped for locking the casing to the sheath element. The shaft portion, the axial coupling and the sonotrode are mutually arranged so that the distal end of the sonotrode may be introduced into a longitudinal opening of the sheath element.

8 Claims, 5 Drawing Sheets

Related U.S. Application Data

(60) Provisional application No. 61/259,383, filed on Nov. 9, 2009, provisional application No. 61/388,243, filed on Sep. 30, 2010, provisional application No. 61/394,580, filed on Oct. 19, 2010.

(51) Int. Cl.
| | | |
|---|---|---|
| *A61B 17/68* | (2006.01) | |
| *A61B 17/70* | (2006.01) | |
| *A61C 8/00* | (2006.01) | |
| *A61B 17/00* | (2006.01) | |
| *A61F 2/28* | (2006.01) | |
| *A61B 17/32* | (2006.01) | |
| *A61C 19/06* | (2006.01) | |

(52) U.S. Cl.
CPC .... *A61F 2/2846* (2013.01); *A61B 17/320068* (2013.01); *A61B 17/866* (2013.01); *A61B 2017/8655* (2013.01); *A61C 19/063* (2013.01); *A61F 2002/285* (2013.01)

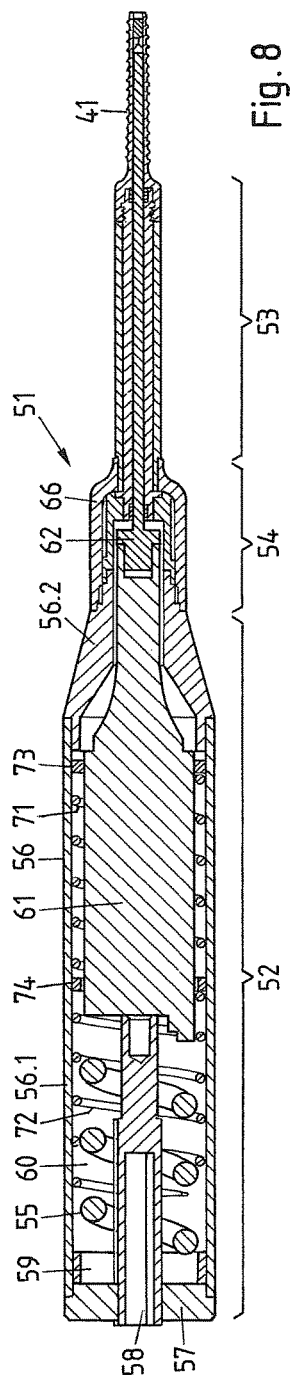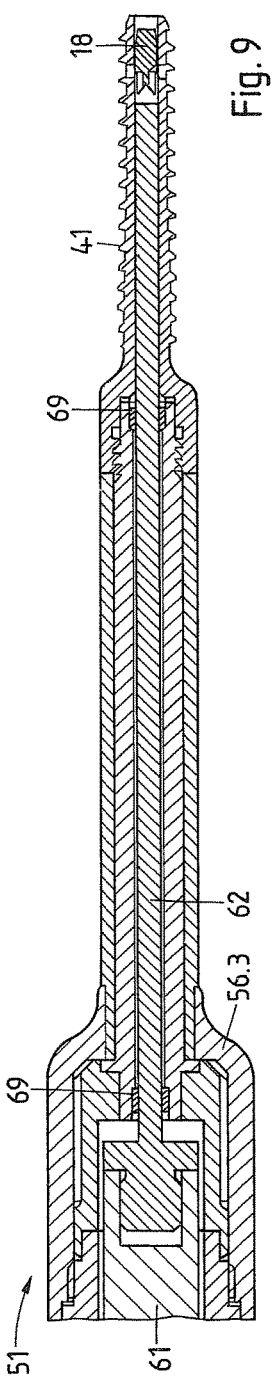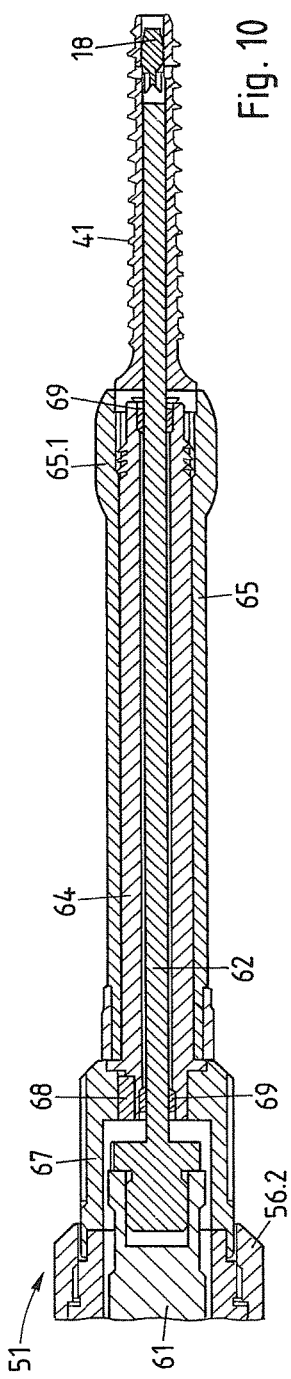

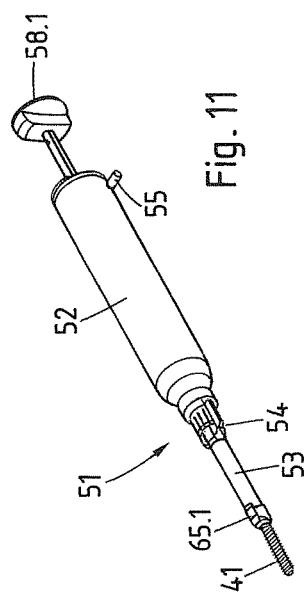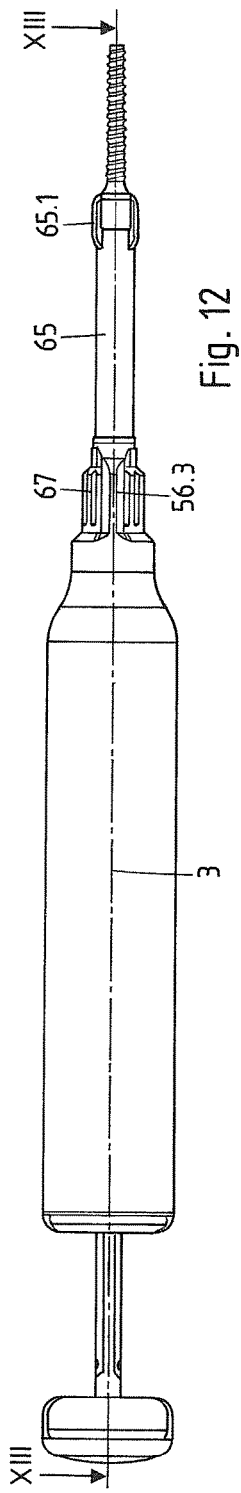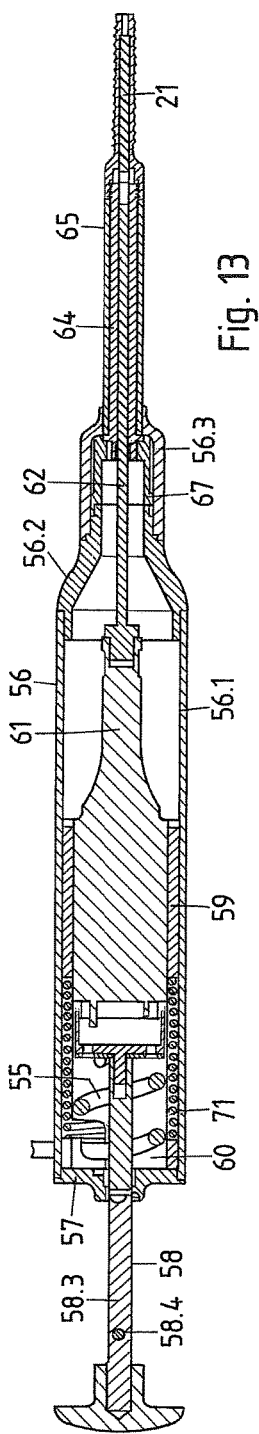

MEDICAL APPARATUS, AND SURGICAL METHOD

BACKGROUND OF THE INVENTION

Field of the Invention

The invention is in the field of medical technology. In particular, it relates to medical devices, medical apparatus and medical methods, especially to implants, apparatuses for implantation, and implantation methods.

Description of Related Art

If screws are anchored in live bone tissue, often the problem of insufficient bone stability or insufficient stability of the anchoring in the bone arises. Especially, in trabecular bone tissue, any load acting on the screw is passed over to only few trabeculae, with adverse consequences both for the load bearing capability of the screw-bone connection and for its long-time stability. This is especially severe in osteoporotic or osteopenic or otherwise weakened bone tissue.

One solution of this problem is the use of an alternative anchoring method that is suitable also for tissue in which screws are not stable. The publications WO 02/069817, WO 2004/017 857, WO 2008/034 277, and WO 2009/055 952 concern anchorage of an implant in bone tissue with the aid of mechanical vibration and a thermoplastic material which is liquefiable by the mechanical vibration, i.e. the thermoplastic material is capable of being liquefied when vibrated and simultaneously kept in contact with a non-vibrating surface. The thermoplastic material, where in contact with the bone tissue, is liquefied and pressed into pores or cavities of the bone tissue to constitute, when re-solidified, a positive fit connection with the bone tissue.

A special group of embodiments of implants and implant anchoring processes is based on the liquefiable material being inserted (pre-assembled or inserted in situ) in a longitudinal bore of a sheath element. The sheath element comprises at least one hole in the sheath element wall, through which the liquefied material is pressed from the longitudinal bore into the structures (pores or cavities or other structures) of the bone tissue or other hard tissue or hard tissue replacement material in which anchoring is desired. This principle of pressing liquefied material out of a tube or sleeve element with lateral openings is for example described in U.S. Pat. No. 7,335,205, U.S. Pat. No. 6,921,264, WO 2009/055 952, WO 2009/010247, WO 2009/010234, and PCT application No. PCT/CH 2009/000138, all of which are incorporated herein by reference.

BRIEF SUMMARY OF THE INVENTION

It is an object of the present invention to provide an apparatus, a medical device and a method overcoming drawbacks of prior art apparatuses, methods and devices.

It is another object of the invention to provide an apparatus for carrying out an implantation or augmentation process with the aid of mechanical vibration and a thermoplastic material which is liquefiable by the mechanical vibration.

In accordance with an aspect of the invention, an apparatus for implanting a medical device in hard tissue and/or hard tissue replacement material or for carrying out an augmentation process in hard tissue and/or hard tissue replacement material is provided. More in particular, the apparatus is equipped for co-operating with a medical device (implant or augmentation device) that comprises a device body with a longitudinal opening (longitudinal bore) extending from a proximal end to a distal direction and one or more holes from the longitudinal bore outward, so that mechanical vibrations coupled into liquefiable (especially thermoplastic) material in the longitudinal bore and the simultaneous application of a pressing force into the distal direction causes portions of the liquefiable material to be liquefied and pressed out of the longitudinal opening through the at least one hole. In this text, such the body of the medical device having the longitudinal hole is also referred to as "sheath element". If the sheath element is in an opening in hard tissue and/or hard tissue replacement material when liquefiable material is liquefied and pressed out of the longitudinal opening through the at least one hole, then the material pressed out of the hole(s) is pressed into structures of the hard tissue/hard tissue replacement material and after re-solidification anchors the sheath element in the hard tissue/hard tissue replacement material and/or augments the hard tissue/hard tissue replacement material.

The apparatus comprises a casing, and, inside the casing, a converter for generating mechanical vibrations when appropriately energized. A sonotrode is coupled to the converter. The converter is slidingly mounted within the casing to be displaceable along a longitudinal direction within the casing. The apparatus further may comprise a spring mechanism that, when tensioned, is capable of moving the sonotrode to a distal direction, to excerpt the pressing force of the sonotrode on an element comprising the liquefiable material of the medical device, and to thereby ensure the necessary propulsion of the sonotrode during the process.

The use of a spring mechanism for this purpose has the advantage that the pressing force is pre-defined. The spring mechanism may be pre-tensioned manually, and in the tensioned position, the position may be fixed by an appropriate means, such as a distance holder between a lamping lever grip and the casing, or by a bayonet fitting like mechanism.

The apparatus further comprises a retention structure that is rotationally coupled to the casing, i.e. not rotatable relative to the casing around the implantation axis. The retention element cooperates with an according not rotationally symmetric element of the medical device to rotationally couple the casing to the sheath element. Furthermore, the apparatus comprises an axial coupling to a sheath element. At least one of the retention structure, of the axial coupling, and of the interplay between the retention structure and the axial coupling preferably also angularly couples the sheath element to the casing, i.e. ensures an angularly stable connection.

The retention structure may be formed by a shaft portion within which the sonotrode is guided. For serving as a retention structure, the shaft portion may have a distal end section that has structures that are not rotationally symmetric around the axis and that cooperate with accordingly fitting structures of the sheath element. For example, the sheath element may have, towards its proximal end, a not rotationally symmetric outer structure such as a flattening so that the surface has two parallel planes, a hexagonal cross section etc. The shaft portion may have a corresponding inner surface, such as of shaft projections engaging the parallel planes, an inner hexagonal structure etc. The shaft portion may then be shifted, by an axial movement, onto the sheath element, whereafter the axial coupling is used to fix the sheath element to the shaft portion. By the effect of such a sheath element outer surface and a shaft portion inner surface, the relative angular position is also stabilized at least with respect to deflections in one plane.

In accordance with an option, the axial coupling may be a coupling thread. To this end, the shaft portion may encase a directing tube with a thread at its distal end. The directing tube may be rotatable relative to the casing by manual or automated rotation. The directing tube may be arranged inside the shaft portion and surround the sonotrode. Alternatively, the guiding tube may surround the shaft portion (in which case the directing tube may comprise an inner thread engaging with an outer thread of the sheath element, whereas the retention structure engages the proximal end of the sheath element's head portion from an inside). For manual rotation, a turning grip may be present that is rotationally coupled to the directing tube. The retention structure then prevents rotation of the sheath element when the latter is screwed onto or into the thread of the directing tube.

In accordance with an alternative option, the axial coupling may be a bayonet like coupling. Also in accordance with such an alternative option, the shaft portion may encase a directing tube rotatable relative to the shaft portion, optionally with a turning grip. The directing tube may cooperate with a fastening mechanism of the sheath element to axially couple the latter to the apparatus upon a twist movement of the directing tube.

In accordance with yet other alternative options, the retention structure may comprise a radially movable element that is brought into contact with the sheath element after the sheath element and the apparatus are brought into the correct relative position. In these alternative options, the retention structure may comprise the axial coupling so that no separate element ranging from a position where it is accessible for the surgeon to the sheath element is required. For example, the retention structure may comprise an inwardly protruding element that engages into an indentation—such as a groove—of the sheath element after the radially movable element has been brought into contact with the sheath element. For example, the retention structure may comprise two or more jaws with a non-circular inner surface of which at least one is swivelling. The jaws may each comprise an inner projecting ridge to form the axial coupling by engaging behind a corresponding indentation of the sheath element—or vice versa. For locking, the pivoting of the jaws relative to one another may be caused by a lever or by an axially movable clamping ring or any other suitable mechanism.

The retention structure and the axial coupling together fix the sheath element to the casing of the apparatus. Such a coupling has proven to be advantageous in many conditions. Together with the spring mechanism or other mechanism ensuring controlled propulsion of the sonotrode during the process, it ensures completely reproducible process conditions.

The retention structure ensures that the sheath element is rotationally coupled to the casing. This brings about a seeming complication, because a coupling between the casing and the sheath element may not be provided by a simple thread—due to the retention structure, it is not possible to just screw the sheath element onto the apparatus. However, it has been found by the inventors that it is often advantageous to firstly implant the sheath element in the tissue, for example by placing it like a conventional bone screw. Thereafter, the orientation is to be kept fix, because too much movement of the sheath element relative to the tissue eases the anchoring and/or unnecessarily damages the tissue. The retention structure makes possible that after placing the sheath element, the apparatus is brought into position, and firmly coupled to the sheath element so that in a subsequent process that comprises coupling energy into a liquefiable element in the longitudinal bore of the sheath element the orientation of the sheath element is controlled by the surgeon.

In a group of embodiments, the spring mechanism comprises a first, helical spring that is arranged around a circumferential surface of the converter and a second spring. The converter is guided within the casing by a first and a second slide bearing. The second slide bearing is mounted slidingly with respect to both, the converter and the casing. The first, helical spring excerpts the spring force between the converter—or an element fixedly mounted thereto, for example the first slide bearing—and the second slide bearing. The second spring excerpts the spring force between the second slide bearing and the casing or an element fixedly mounted thereto, such as a cap.

The first slide bearing may be a converter ring surrounding the converter at a distal position and for preferably fixedly mounted thereto. The second slide bearing may be a sliding ring surrounding the converter at a more proximal position, which position is dependent on the deflection of the first spring. The first spring may be arranged to excerpt the first spring force between the first slide bearing and the second slide bearing. The second spring may be arranged to excerpt the second spring force between the second slide bearing and a cap fixedly mounted to the casing. The first spring may be a helical spring encompassing a converter body of the converter.

Generally, in an apparatus with a converter slidingly mounted within a casing, the converter needs to be guided along a substantial portion of its length (i.e. of its proximo-distal extension), or needs to be guided at two distinct axial positions in order not be subject to undesired pivoting movements (yaw or pitch movements). If the spring is only arranged between the most distal portion of the guiding and the distal end of the casing, as for example taught in WO 2009/010234, then in order to have a spring having an appropriate spring constant and being in its linear regime over the entire range of its deflection, the casing needs to have a length that is substantially greater than the length of the converter to provide sufficient space and travel for the spring that is arranged distally of the converter.

The approach according to the group of embodiments of the invention, in contrast, features the advantage that for a given pre-set deflection—which may correspond to the length of a liquefiable element that is a polymer pin to be liquefied in a sheath element—a total spring extension may be essentially the axial extension of a converter body plus of the space distally of the converter. Put simply, a spring mechanism (comprising the first and second spring in series) of a much longer axial extension can be used for a given casing extension. This brings about additional degrees of freedom in choosing the appropriate springs and thus engineering the travel and pressing force, which are often important parameters in the implantation or augmentation process.

In another group of embodiments, the converter is guided in the casing by an axially extended bushing that is, for example, fixed to the converter. The spring mechanism may then engage with the proximal end of the bushing, or alternatively, with the proximal end of the converter.

In even further embodiments, the movement of the converter relative to the casing is brought about by a mechanism different from a spring mechanism, such as for example by an electrical motor.

The apparatus may in addition to the casing with the converter, sonotrode and the hereinbefore described elements also comprise an electronic module that is connected to the converter by a cable. The electronic module produces an electric signal of the frequency desired for the mechanical vibrations (for example ultrasonic frequency) and further may have a feedback control mechanism that adapts the frequency to the actual situation, for example depending on the mechanical load. The electronic module is generally external to the casing, and the cable therefore goes through an opening in the casing. In accordance with embodiments of the invention, the casing comprises a cable storage that stores a portion of the cable, the length of which is enough to compensate for the entire travel of the converter from the retracted position to the most extended position—so that the cable does not need to follow the travel by sliding through the opening in the casing.

In embodiments with a spring, the apparatus may have at least one of the following:
- an operating lever for manually retracting the converter with the sonotrode against the spring force. Such operating lever may comprise a hand grip or similar.
- a holding mechanism that holds the converter with the sonotrode in the retracted position until the mechanism is released. For example, the holding mechanism may comprise a tilt lever, a distal end of which may rest against the casing.

The invention further concerns an assembly of an apparatus of the herein described kind with an implant or augmentation element of the herein described kind, wherein a head portion of the implant or augmentation element is adapted to the retention and coupling structure of the apparatus.

Also a method of implanting an implant is provided. The method is for example suitable for implanting a bone screw, especially a pedicle screw, but also another bone screw. It is further suitable for implanting an implant without an outer thread. For example, it is suitable for implanting an implant of the kind described in U.S. patent application 61/394,580 incorporated herein by reference in its entirety.

The method comprises the steps of:
- providing the implant with an implant shaft portion and an implant head portion, the implant head portion being rotationally asymmetric, the implant shaft portion having a longitudinal bore and at least one opening ranging from the longitudinal bore to an outside;
- driving the shaft portion into bone tissue so that the head portion protrudes from the bone tissue;
- after driving the shaft portion into bone tissue, coupling an apparatus of the kind described hereinbefore to the head portion, with thermoplastic material being in the longitudinal opening and with the orientation of the implant head portion being fixed relative to the casing of the apparatus by the retention structure;
- energizing the converter to cause the sonotrode to couple mechanical vibrations into the thermoplastic material while causing the sonotrode to be pressed towards the distal direction and thereby causing portions of the thermoplastic material to be liquefied and pressed out of the at least one hole into structures of the bone tissue, and
- causing the converter to stop and removing the apparatus.

Embodiments of devices and methods in accordance with the invention may be devices/methods for human surgery, or alternatively for (non-human) animal surgery, especially for surgery of dogs, cats or other pets.

Mechanical vibration or oscillation suitable for devices and methods according to embodiments of the invention that include liquefaction of a polymer by friction heat created through the mechanical vibration has preferably a frequency between 2 and 200 kHz (even more preferably between 10 and 100 kHz, or between 20 and 40 kHz) and a vibration energy of 0.2 to 20 W per square millimeter of active surface. The vibrating element (sonotrode) is e.g. designed such that its contact face oscillates predominantly in the direction of the element axis (longitudinal vibration) and with an amplitude of between 1 and 100 μm, preferably around 10 to 30 μm. Rotational or radial oscillation is possible also.

For specific embodiments of apparatuses, it is possible also to use, instead of mechanical vibration, a rotational movement for creating the named friction heat needed for the liquefaction of the anchoring material. Such rotational movement has preferably a speed in the range of 10,000 to 100,000 rpm. A further way for producing the thermal energy for the desired liquefaction comprises coupling electromagnetic radiation into one of the device parts to be implanted and designing one of the device parts to be capable of absorbing the electromagnetic radiation, wherein such absorption preferably takes place within the anchoring material to be liquefied or in the immediate vicinity thereof. Preferably electromagnetic radiation in the visible or infra-red frequency range is used, wherein the preferred radiation source is a corresponding laser. Electric heating of one of the device parts may also be possible.

In this text the expression "thermoplastic material being liquefiable e.g. by mechanical vibration" or in short "liquefiable thermoplastic material" or "liquefiable material" is used for describing a material comprising at least one thermoplastic component, which material becomes liquid or flowable when heated, in particular when heated through friction i.e. when arranged at one of a pair of surfaces (contact faces) being in contact with each other and vibrationally or rotationally moved relative to each other, wherein the frequency of the vibration is between 2 kHz and 200 kHz, preferably 20 to 40 kHz and the amplitude between 1 μm and 100 μm, preferably around 10 to 30 μm. Such vibrations are e.g. produced by ultrasonic devices as e.g. known for dental applications. For being able to constitute a load-bearing connection to the tissue, the material at the time of insertion has an elasticity coefficient of more than 0.5 GPa, preferably more than 1 GPa. The elasticity coefficient of at least 0.5 GPa also ensures that the liquefiable material is capable of transmitting the ultrasonic oscillation with such little damping that inner liquefaction and thus destabilization of the liquefiable element does not occur, i.e. liquefaction occurs only where the liquefiable material is at the liquefaction interface to the stop face. The plastification temperature is preferably of up to 200° C., between 200° C. and 300° C. or even more than 300° C. Depending on the application, the liquefiable thermoplastic material may or may not be resorbable.

Suitable resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers. Examples of suited thermoplastic material include any one of the polylactide products LR708 (amorphous Poly-L-DL lactide 70/30), L209 or L210S by Böhringer Ingelheim.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate® by DSM, especially Bionate 75D and Bionate 65D; according information is available on datasheets publicly accessible for example via www-.matweb.com by Automation Creations, Inc.). An overview table of polymers and applications is listed in Wintermantel, page 150; specific examples can be found in Wintermantel page 161 ff. (PE, Hostalen Gur 812, Hochst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff. (POM-Polyacetal, tradenames Delrin, Tenac, has also been used in endoprostheses by Protec).

The liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

If the liquefiable material is to be liquefied not with the aid of vibrational energy but with the aid of electromagnetic radiation, it may locally contain compounds (particlulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see SM Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 µm (contents, preferentially 10-25% by volume), sub-micron (nanofillers as from precipitation, preferentially plate like aspect ratio>10, 10-50 nm, contents 0.5 to 5% by volume).

A specific example of a material with which experiments were performed was PLDLA 70/30 comprising 30% (weight percent) biphase Ca phosphate that showed a particularly advantageous liquefaction behaviour.

The material of the sheath element (which may be a screw) may be any material that does not melt at the melting temperatures of the liquefiable material. Especially, the sheath element may be of a metal, for example a titanium alloy. A preferred material is titanium grade5. This material, in addition to being generally suited for implantable devices, has a comparably low heat conduction. Because of this bad heat conduction, the melting zone arising in liquefiable material and at the interface to the directing structure is heated quickly, without the surroundings being heated to too high temperatures. Alternative materials for the sheath element are other metals like other titanium alloys, stainless steel, ceramics like Zirconium oxides or Aluminum oxides, or hard plastics such as PEEK etc.

BRIEF DESCRIPTION OF THE DRAWINGS

In the following, ways to carry out the invention and embodiments are described referring to drawings. The drawings mostly are schematical. In the drawings, same reference numerals refer to same or analogouos elements. The drawings show:

FIGS. 7-10 a first embodiment of an apparatus for automated implantation or augmentation;

FIGS. 11-15 a second embodiment of an apparatus for automated implantation or augmentation.

DESCRIPTION OF THE PREFERRED EMBODIMENTS

Figure 1:
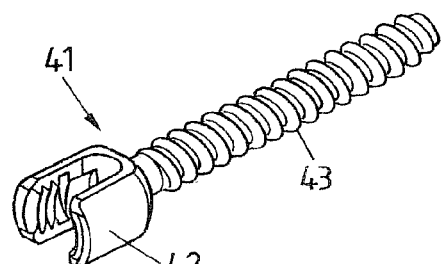
FIGS. 1-3 a pedicle screw being an embodiment of a medical device implantable by an apparatus according to an aspect of the invention.
Figure 2:
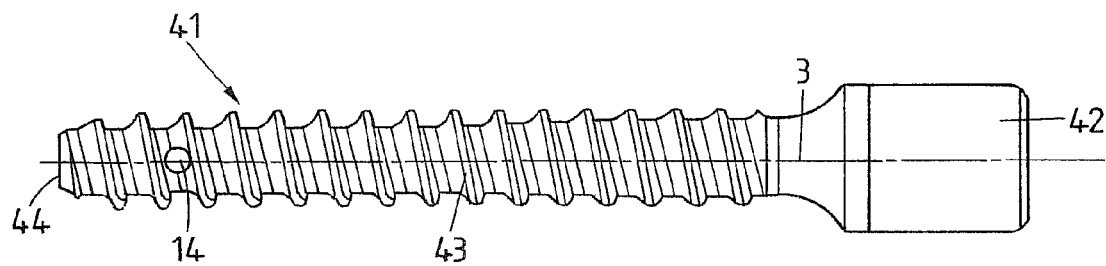
Figure 3:
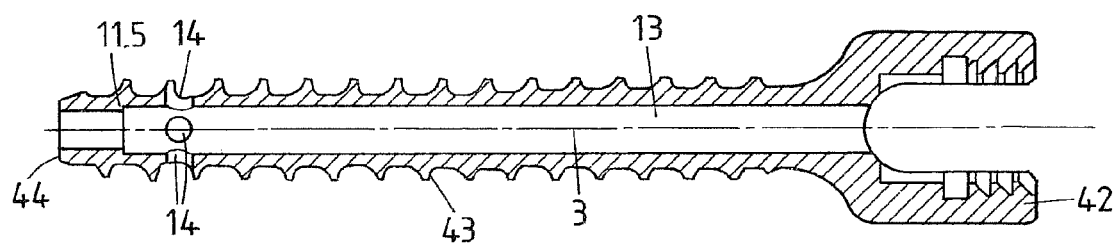
Figure 4:
FIG. 4 a liquefiable element for the pedicle screw of FIGS. 1-3.

The device 41 schematically depicted in FIGS. 1-6 is a surgical implant for being anchored in hard tissue and/or hard tissue replacement material. More in particular, it is a pedicle screw.

In alternative embodiments, the device may have another function similar to the function of a surgical screw, and/or of an anchor (such as a suture anchor or an implant to which a dental crown is to be mounted), or it may have a "stand-alone" function, for example by containing a substance to be delivered to a surrounding tissue, and/or by containing a different device such as an electronic device, etc. Like in all other embodiments of the invention, the device, if being designed to remain in the patient's body after surgical operation, may have any function a surgical device anchored in hard tissue and/or hard tissue replacement material may have in surgery. As an alternative to being designed to remain the patient's body after the surgical operation, the devices according to the different embodiments—unless explicitly stated otherwise—may also be a temporary anchor or may be an augmentation device, for example as taught hereinafter.

The device 41 is insertable into an opening or a gap or the like of hard tissue and/or hard tissue replacement material, essentially by a movement along an implantation axis 3 that is also considered to be a longitudinal axis of the device. The device comprises a wall portion 11.1 that surrounds a longitudinal bore 13 open to the proximal side. A plurality of holes 14 (four holes equally distributed around the circumference in the depicted embodiment) range from the longitudinal bore radially outward.

The device further comprises a liquefiable element 21, namely a polymer pin 21 that is adapted to the sheath element to be inserted in the longitudinal bore 13 from the proximal side.

The device, or more in particular, the pedicle screw 41 comprises a screw head 42, a threaded section 43, and a distal end portion 44. The pedicle screw further comprises a longitudinal through bore 13 that, towards the distal end, comprises a narrowed portion so that a shoulder 11.5 for stopping the insert element (not shown) inserted from the proximal side is formed.

The thread has a constant outer diameter (major diameter), whereas a core diameter (minor diameter) is larger at the proximal side than at the distal side. More concretely, in the depicted embodiment, in a central portion of the threaded section the core diameter gradually reduces, whereas in peripheral portions the core diameter is constant. In other, alternative embodiments, the core diameter is constant, is gradually reduced along the entire length of the threaded section, or the core diameter has a stepped characteristic as taught in WO 90/02526, or has any other characteristics. Also, the outer diameter of the threaded section need not be constant. Generally, the approach according to the first aspect of the invention may be combined with any suitable outer thread. Compared to prior art pedicle screws with a longitudinal bore, the bore diameter is comparably large to make insertion of the liquefiable element—that may be a polymer pin—possible. In the depicted embodiment, the bore diameter at the more proximal portion of the threaded section is 3.1 mm and at the distal portion of the threaded section is 2.9 mm, whereas the major diameter is 6.6 mm and the minor diameter is between 4.4 mm and 5.3 mm. The resulting wall strength has proven to be sufficient.

The screw head is flattened and comprises an inner thread that can be used for coupling to an apparatus for automated insertion, as described hereinafter.

The longitudinal bore 13 is a through bore, making the device suitable for being guided by a wire in minimally invasive surgery. The through bore is narrowed towards the distal side so that a shoulder 11.5 is built. The shoulder serves as a stop structure for an insert element 18 that terminates the longitudinal opening for the liquefiable element towards the distal side.

Figure 5:
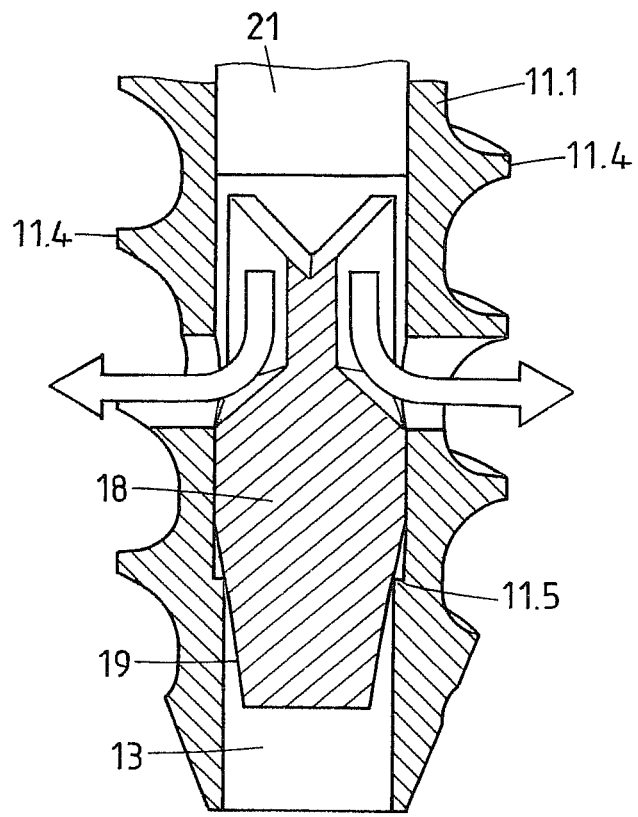
FIGS. 5 and 6 an insert element for the pedicle screw of FIGS. 1-3.
Figure 6:
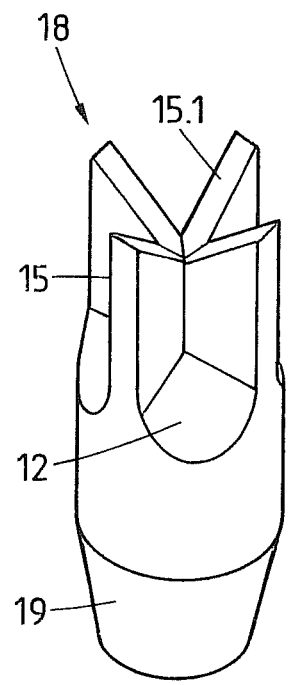

As shown in FIGS. 5 and 6, the insert element comprises an optional directing structure including walls 15 and the ramp portions 12. The insert element comprises a distal tapered portion 19 that together with the shoulder 11.5 co-operates to form a force fit. The optional directing structure comprises a ramp portion 12 sloping away in a concave manner from a center around the longitudinal axis. At the radially outer side of the ramp portion, the wall portion of the device has the holes 14. At angular positions between the holes, the directing structure further comprises walls 15 having a proximal edge 15.1 and angularly subdividing a portion of the longitudinal bore volume communicating with the holes 14.

For the anchoring or augmenting process, the liquefiable element 21 is inserted and brought into a position where it abuts against the directing structure (or other structure at least partly limiting the longitudinal bore towards the distal side). While the sheath element is in contact with hard tissue and/or hard tissue replacement material, the liquefiable element is pressed against the directing structure while energy impinges from the proximal side. Under the additional effect of the pressing force, the liquefied material of the liquefiable element is pressed out through the holes 14 and into structures, like pores, surface unevenness, inhomogeneities etc. of the hard tissue and/or hard tissue replacement material.

In the anchoring and/or augmentation process, a sonotrode is used to couple the energy into the liquefiable element. To this end, the sonotrode is pressed against a proximal end face of the liquefiable element while mechanical vibrations are coupled into the sonotrode. The mechanical vibrations are coupled into the liquefiable element 21, and the vibration energy is at least partly absorbed at the interface to the directing structure—or other distal stop structure—causing the polymer material of the liquefiable element to at least locally liquefy at this interface. Liquefied and re-solidifying material portions pressed into the surrounding bone tissue and interpenetrating structures of the latter strengthen the tissue that may be cancellous bone or according replacement material. In addition, if the device is an implant meant to remain in the patient's body and portions of the liquefiable material remain, after re-solidifying, in the sheath element, the connection provides a solid anchoring.

Figure 7:
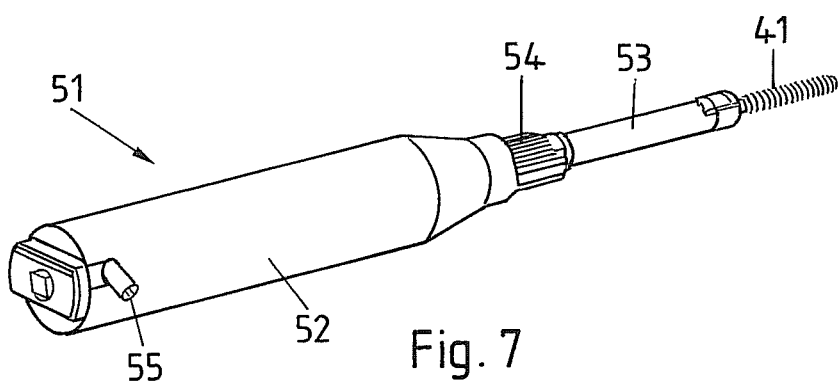
Figure 14:
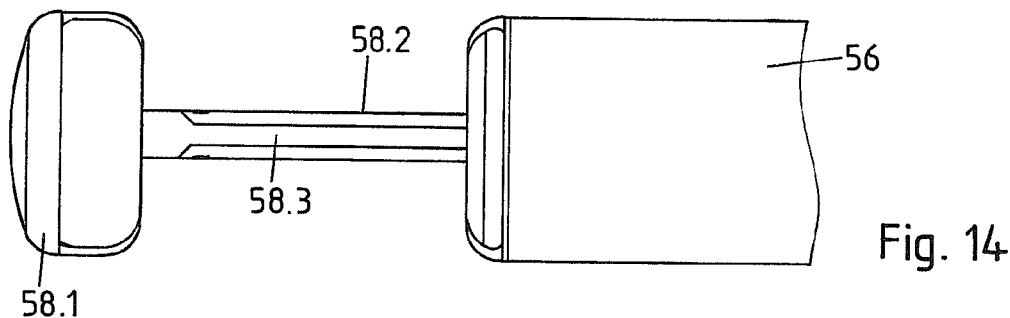
Figure 15:
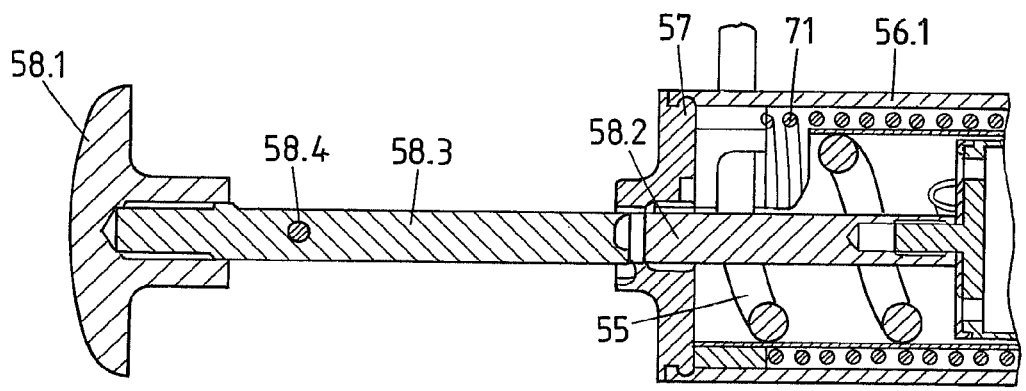

FIGS. 7 and 8 depict an apparatus 51 for automated implantation of a medical device or for automated augmentation. In the figures, a bone screw 41, namely a pedicle screw as illustrated in FIGS. 1-5 is coupled to the apparatus 51.

FIGS. 9 and 10 show, in longitudinal horizontal and vertical sections, an enlarged detail of a distal end of the apparatus 51, with a bone screw 41 of the kind illustrated in FIGS. 10-12 coupled thereto.

The apparatus 51 comprises a handle portion 52, a shaft portion 53, and an intermediate operating knob portion 54. In FIG. 8, also an electricity supply cable 55 is depicted. The electricity supply cable may connect the handle portion comprising the converter with a (not shown) electronic module that supplies an electrical signal used for energizing the converter. The electrical signal may have the frequency and amplitude required for the process.

Proximally of the ultrasonic converter, a free space within the casing forms a cable storage 60. The cable is coiled up in the cable storage in a manner that upon movement of the converter back and forth between the retracted position and the distal position shown in FIGS. 7-10, the length of the cable portion that is within the casing 56 remains constant. This brings about a substantial advantage during delicate surgical operations, since the surgeon does not need to guide the cable into the casing during the advancement movement of the converter and the sonotrode.

For example, the cable may be wound up in the cable storage in a helical manner as depicted in the figures.

The handle portion has a handle casing 56 and a cap 57 closing the latter off proximally. The casing comprises a tube portion 56.1 and a taper portion 56.2. A clamping lever 58 reaches through the cap and is used to pre-load the apparatus by retracting the ultrasonic converter 61 arranged inside the casing 56. A cable clamp 59 for the electricity supply cable 55 is arranged next to the cap 57. The sonotrode 62 is coupled to the converter 61 and is guided within the shaft 65 by a directing tube 64 that comprises two slide bushes 69 bearing and guiding the sonotrode 62. The directing tube 64 is rotationally coupled to a turning grip 67 by means of a fitting key 68. The turning grip and the directing tube are rotatable relative to the casing 56 and the shaft 65 by manual operation. The taper portion 56.2 of the casing has two projecting prongs 56.3 overlapping the turning grip 67 and rotationally fixing the shaft 65 to the casing 56. The directing tube 64 comprises, at its distal end, an outer thread cooperating with the inner thread of the screw head. The screw is mountable onto the apparatus by firstly positioning the screw at the distal end of the shaft, while shaft projections 65.1 overlap the flattened portions of the screw head (see FIG. 10) to hold the bone screw 41, and secondly rotationally moving the turning grip 67 to cause the outer thread of the directing tube to engage into the inner thread of the screw head.

This mounting of the screw is effected while the ultrasonic converter 61 is in the retracted, pre-loaded position (not shown in FIGS. 7-10) and when a liquefiable material pin (also not shown in FIGS. 7-10) is in the longitudinal bore of the screw, for example by being attached to the distal end of the sonotrode or by being pre-assembled with the bone screw.

The anchoring or augmentation process is initiated while a possible holding mechanism holding the clamping lever in the retracted position—such as a removable distance holder placed proximally of the cap 57 or a bayonet fitting like mechanism for the clamping lever—is released and the converter 61 generates mechanical vibrations of the sonotrode 62. In the retracted position of the clamping lever 58, the converter 61 and the sonotrode 62, two springs are compressed against a spring force. In the depicted embodiment both springs are helical springs, the first spring 71 arranged around the converter 61.

The first spring 71 is arranged between a distal converter ring 73 and a proximal sliding ring 74. The converter ring 73 is fixedly attached to the converter 61 and slidingly mounted in the casing 56. The sliding ring 74 is also mounted to encompass the converter—near a distal end thereof—but is sliding both, relative to the converter 61 and relative to the casing 56. The second spring 72 is arranged between the sliding ring 74 and the cap 57 (or another element fixed relative to the casing). In the retracted position, the converter ring 73 is deflected from the position shown in the figures by the full displacement of the converter. The sliding ring 74 is also deflected, by about half of the full deflection—depending on the ratio of the overall spring constant of the first and second spring in series to the spring constant of the first spring.

During the implantation or augmentation process, the springs 71, 72 act to impinge the sonotrode with a predefined pressing force in the distal direction.

Another embodiment of the apparatus is shown in FIGS. 11-15. FIGS. 11-15 show the apparatus in a configuration with a pedicle screw loaded by a thermoplastic element 21 while the ultrasonic converter 61 is in the retracted, pre-loaded position. The embodiment illustrated in FIGS. 11-15, is distinct from the one of FIGS. 7-10 in that it has the following features:

instead of two springs, only a single, helical spring 71 is present. A single, axially extended bearing bush 59 replaces the two bearings of the previous embodiment.

The clamping lever 58 has a holding mechanism that holds it in the pre-tensioned state. The retaining mechanism comprises a tilt lever 58.3 that is coupled to the handgrip 58.1 and pivoting relative to a lever shaft 58.2 around a pivoting axis 58.4. The lever shaft is coupled to the converter 61. The distal end of the tilt lever 58.3 may rest against the cap 57 when the clamping lever 58 is in the retracted position and the tilt lever 58.3 is tilted away from the position shown in FIG. 15 by a few degrees so that the tilt lever serves as distance holder that holds the converter and the sonotrode in the retracted position. When the surgeon is ready to start the liquefaction process, she/he pushes the clamping lever 58 slightly back into the proximal direction and tilts the tilt lever back into the position of FIG. 15, whereafter the spring 71 may press the converter 61 with the sonotrode 62 towards the distal direction and thereby excerpt the pressing force on the thermoplastic element 21.

In embodiments of the kind described referring to FIGS. 7-15, instead of a thread, a directing tube or other element rotatable relative to the shaft could also be used for a bayonet coupling. For example the directing tube could comprise one or two projections that can be brought into engagement with an inner groove of the sheath element, for example by a quarter of a turn.

Figure 16:
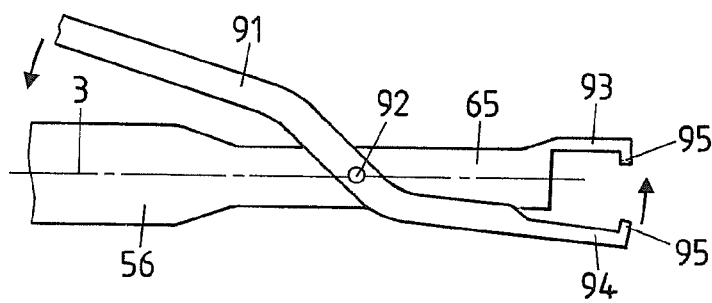
FIGS. 16-18 alternative retention structures.
Figure 17:
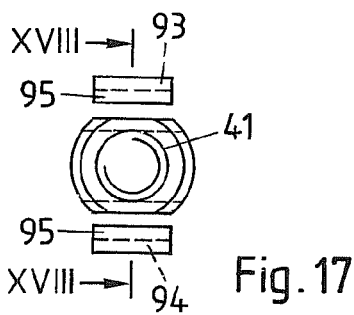
Figure 18:
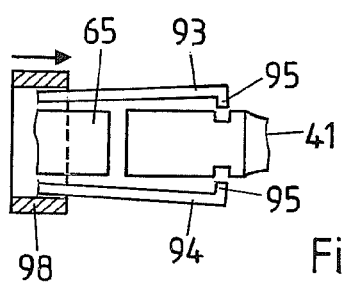

FIGS. 16-18 yet very schematically depict alternative combinations of a retention structure with an axial coupling. In the variant of FIG. 16, a first jaw 93 of the retention structure is fixedly connected to the shaft 65, as the shaft projections in the previously described embodiments. A second jaw 94 belongs to a lever 91 that is swiveling about a swiveling point 92 so that the surgeon may, by operating the lever, move the second jaw radially inward as shown by the arrows in the figure, and thereby bring the retention structure into engagement with the not rotationally symmetric portion of the sheath element (such as the flattened head of the pedicle screw 41 described in the previous embodiments). In contrast to the previous embodiments, the jaws then may comprise an axial coupling protrusion 95 that engages in an according indentation of the sheath element or vice versa. Due to this, there is no need for a separate directing tube (or other means rotatable relative to the shaft 65) of a thread or bayonet coupling between the apparatus and the sheath element.

Both jaws, like in the previously described embodiments, comprise inner (i.e. facing to the axis) surfaces that are not rotationally symmetric.

FIG. 17 shows a view of two jaws 93, 94 adjacent the flat portions of the head of the screw 41.

Instead of by a lever 91 as depicted in FIG. 16, the jaws 93, 94 may be brought into engagement with the screw head also by other mechanisms, such as by the mechanism shown in FIG. 18. FIG. 18 very schematically depicts a section along the line indicated by the arrows in FIG. 17. The jaws can be deflected against an elastic force, for example, by axially moving a deflecting ring 98 in the direction of the arrow. A (not shown) clipping mechanism or similar may hold the deflecting ring in its position once it has been moved. The embodiment of FIG. 18 may comprise two or more jaws.

The embodiments of the invention hereinbefore have been illustrated referring to bone screws with fixed head portions. However, the invention also works for different kinds of implants or augmentation devices that have a sheath element and are equipped for releasing a thermoplastic material, in a liquefied state, into surrounding tissue/tissue replacement material.

For example, an important class of medical implants is bone screws with a multi-axial head. In such bone screws, the head, in a non-mounted state, is swiveling relative to the screw shaft. The bone screws may comprise a clamp mechanism that fixes the relative position of head and screw shaft when the screw is under the mechanical load. For example, if the screw is a pedicle screw, the clamp mechanism fixes the relative orientation of head and shaft once the rod is introduced in the head portion and fixed with the clip provided for this purpose.

In embodiments of the apparatus according to the invention, the retention structure engages with the screw's head portion. A projecting element of the apparatus at the same time activates the screw's clamp mechanism (for example by pulling the screw head portion into a proximal direction relative to the screw shaft portion against which latter a for example plane projection is pressed) so that the clamp mechanism fixes the orientation of the screw shaft portion relative to the retention structure.

Various other embodiments are possible. Especially, the skilled person will know many possible rotationally asymmetric structure of a sheath element with which a corresponding structure of the apparatus may engage to form the retention structure.

What is claimed is:

1. A method of implanting an implant into bone tissue, comprising the steps of:
    providing the implant with an implant shaft portion and an implant head portion, the implant shaft portion having a longitudinal bore extending therethrough and at least one opening ranging from the longitudinal bore radially to an outside of the implant shaft portion;
    driving the implant shaft portion into the bone tissue so that the head portion protrudes from the bone tissue;
    coupling an apparatus to the implant, the apparatus comprising a casing and, mounted inside the casing to be displaceable in a longitudinal direction relative to the casing, a converter operable to generate mechanical vibrations, the apparatus further comprising a sonotrode coupled to an output location of the converter, and an apparatus shaft portion with a retention structure that is rotationally coupled to the casing and equipped with at least one projection for cooperating with a rotationally asymmetric element of the implant head portion to rotationally couple the casing to the implant head portion,
    wherein the step of coupling comprises rotationally coupling the casing of the apparatus to the implant in a manner such that the implant is not rotatable relative to the casing around an implantation axis,
    while thermoplastic material is within the longitudinal bore of the implant or extends into the longitudinal bore of the implant, energizing the converter to cause the sonotrode to couple mechanical vibrations into the thermoplastic material while causing the converter and the sonotrode to be pressed towards a distal direction relative to the casing when the casing is rotationally coupled to the implant head portion and thereby causing portions of the thermoplastic material to be liquefied and pressed out of the at least one opening into structures of the bone tissue, and
    causing the converter to stop and removing the apparatus by decoupling the apparatus from the implant.

2. The method according to claim 1, wherein the head portion of the implant is chosen to be rotationally asymmetric.

3. The method according to claim 1, wherein the step of coupling is carried out after the step of driving the implant shaft portion into bone tissue.

4. The method according to claim 1, wherein causing the converter and the sonotrode to be pressed towards the distal direction comprises using a spring to press the converter to the distal direction relative to the casing.

5. The method according to claim 1, wherein the apparatus further comprises a rotatable element rotatable relative to the casing, the step of coupling the apparatus to the implant comprising rotating the rotatable element until the implant is axially coupled to the casing.

6. The method according to claim 5, wherein the implant comprises a thread and wherein rotating the rotatable element causes the implant to be screwed onto the apparatus.

7. The method according to claim 5, wherein the shaft portion rotationally couples the implant to the casing while the rotatable element is rotated.

8. The method according to claim 5, wherein rotation of the rotatable element causes an indentation or projection of the apparatus to cooperate with a projection or indentation of the implant element to form a bayonet coupling.

* * * * *